(12) United States Patent
Scussel et al.

(10) Patent No.: US 8,080,065 B2
(45) Date of Patent: Dec. 20, 2011

(54) VACUUM ASSISTED PROSTHETIC SLEEVE AND SOCKET UTILIZING A DOUBLE MEMBRANE LINER

(75) Inventors: Rick C. Scussel, Newton, AL (US); David Wiley Alford, Dothan, AL (US)

(73) Assignee: Scussel SBJ Systems, LLC, Dothan, AL (US)

( * ) Notice: Subject to any disclaimer, the term of this patent is extended or adjusted under 35 U.S.C. 154(b) by 410 days.

(21) Appl. No.: 11/861,603

(22) Filed: Sep. 26, 2007

(65) Prior Publication Data

US 2008/0221706 A1    Sep. 11, 2008

Related U.S. Application Data (63) Continuation-in-part of application No. 11/762,306, filed on Jun. 13, 2007.

(60) Provisional application No. 60/904,833, filed on Jun. 13, 2007.

(51) Int. Cl.
*A61F 2/78* (2006.01)
*A61F 2/80* (2006.01)
*A61F 2/60* (2006.01)

(52) U.S. Cl. .......... 623/33; 623/32; 623/36; 623/34

(58) Field of Classification Search .......... 623/32
See application file for complete search history.

(56) References Cited

U.S. PATENT DOCUMENTS

| | | | |
|---|---|---|---|
| 4,863,201 A | 9/1989 | Carstens | |
| 4,908,037 A * | 3/1990 | Ross | 623/32 |
| 4,923,474 A | 5/1990 | Kiasson et al. | |
| 5,258,037 A | 11/1993 | Caspers | |
| 5,376,132 A | 12/1994 | Caspers | |
| 5,534,034 A | 7/1996 | Caspers | |
| 5,549,709 A | 8/1996 | Caspers | |
| 5,571,208 A | 11/1996 | Caspers | |
| 5,735,906 A | 4/1998 | Caspers | |
| 5,904,722 A | 5/1999 | Caspers | |
| D429,335 S | 8/2000 | Caspers | |
| 6,508,842 B1 | 1/2003 | Caspers | |
| 6,554,868 B1 * | 4/2003 | Caspers | 623/34 |
| 6,645,253 B2 | 11/2003 | Caspers | |
| 6,726,726 B2 | 4/2004 | Caspers | |
| 6,761,742 B2 | 7/2004 | Caspers | |
| 6,926,742 B2 | 8/2005 | Caspers | |
| 6,974,484 B2 | 12/2005 | Caspers | |
| 7,025,793 B2 | 4/2006 | Egilsson | |
| 7,144,429 B2 | 12/2006 | Carstens | |
| 7,150,762 B2 | 12/2006 | Caspers | |
| 7,169,188 B2 | 1/2007 | Carstens | |
| 7,235,108 B2 | 6/2007 | Carstens | |
| 2004/0143345 A1 | 7/2004 | Caspers | |

* cited by examiner

*Primary Examiner* — David Isabella
*Assistant Examiner* — Jacqueline Woznicki
(74) *Attorney, Agent, or Firm* — The Gache Law Firm, P.C.; Russell C. Gache (57) ABSTRACT

A prosthetic sleeve and socket system, the sleeve including dual flaps or skirts concentrically arranged about the sleeve and configured to form a sealed chamber between the sleeve and socket when the sleeve is inserted into the socket. An air permeable material is interposed between one of the skirts and the sleeve to maintain a continuous interconnected air layer therebetween. An expulsion valve is provided to allow air contained within the sealed chamber to be forced out of the chamber ahead of the sleeve when it is inserted into the socket, and a powered vacuum pump maintains the vacuum thereafter, if needed. The system allows for a substantial reduction in size of known sockets and permits, in some instances, the disposal of bulky suspension straps currently in use to force the socket against a residual limb.

16 Claims, 6 Drawing Sheets

VACUUM ASSISTED PROSTHETIC SLEEVE AND SOCKET UTILIZING A DOUBLE MEMBRANE LINER

This application claims the benefit of filing priority under 35 U.S.C. §119 and 37 C.F.R. §1.78 from U.S. Provisional Application Ser. No. 60/904,833 filed Feb. 5, 2007, for SCUSSEL/SBJ SUCTION LINER-SOCKET, and the non-provisional patent application Ser. No. 11/762,306 filed Jun. 13, 2007, for VACUUM ASSISTED PROSTHETIC SLEEVE AND SOCKET. All information disclosed in those prior applications is incorporated herein by reference.

FIELD OF THE INVENTION

This invention relates to a prosthetic sleeve and socket combination, and more particularly, to a prosthetic sleeve having dual flaps or skirts concentrically arranged about the sleeve and configured to form a sealed chamber between the sleeve and socket when the sleeve is inserted into the socket.

BACKGROUND OF THE INVENTION

An amputee is a person who has lost part of an extremity or limb such as a leg or arm. That which remains is commonly referred to as a residual limb. Residual limbs come in various sizes and shapes with respect to the stump. For instance, new amputations are often slightly bulbous or cylindrical in shape while older amputations that have atrophied are generally more conical in shape. Residual limbs may also be characterized by their various individual configurations including the volume and shape of a stump, bony prominence, uneven limb volume or soft tissue configurations. For example, a leg severed above the knee generally terminates in a fleshy stump while a leg severed below the knee generally terminates in a bony stump.

More particularly, referring to FIG. 1, a below the knee residual limb 18 is shown and described as a leg 20 having been severed below the knee terminating in a stump 22 also referred to as a leg terminus. In this case stump 22 is formed by the severed tibia 28 and fibula 30 and the smaller, less voluminous muscles of the lower leg. Thus, a below the knee residual limb 18 has its stump 22 generally characterized as being a more bony structure while an above the knee residual limb (not shown) is characterized as including more soft tissue.

Artificial limbs typically used by a leg amputee have sockets to put the amputee's stump into. There are generally two categories of sockets. There are hard sockets wherein the stump goes right into the socket actually touching the socket wall without any type of liner or stump sock. Another category of sockets is a socket that utilizes a liner or insert. Both categories of sockets typically are opened ended sockets having a hollow chamber in the bottom.

In the past, most artificial limbs were suspended from the amputee's body by some form of pulley, belt or strap suspension often used with various harnesses, leather lacers or lacings. However, these types of suspension systems are bulky and uncomfortable to wear, and when the residual limb was a leg severed above the knee, the socket had to include an ischial flare which only increased bulk and discomfort. Another method of suspending artificial limbs required the amputee to use a latex rubber tube formed into a rubber-like sleeve which would be rolled on over both the top of the artificial limb and onto the amputee's thigh. In some instances, a negative pressure system was used in combination with the rubber sleeve which required forming a negative pressure chamber between the leg and socket using a vacuum pump. The sleeve acted as a seal between the limb and socket thereby suspending the socket from the limb. However, since the seal was formed on the outside of the socket it was prone to puncturing which resulted in suction loss within the sealed chamber and detachment of the socket from the residual limb.

SUMMARY OF THE INVENTION

The present invention is directed to a prosthetic sleeve and socket system, and more particularly, to a prosthetic sleeve having dual skirts or flaps concentrically arranged about the sleeve and configured to form a sealed chamber between the sleeve and socket when the sleeve is inserted into the socket. In addition, a method of attaching a prosthesis to a residual limb is presented consisting of placing the improved prosthetic sleeve with dual skirts about a residual limb, inserting the residual limb and prosthetic sleeve into a socket conforming to the shape of the residual limb, forming a continuous seal between the sleeve and an interior surface of the socket, evacuating air from a chamber contained between the residual limb and an interior surface of the socket and creating a partial vacuum within the chamber sufficient to maintain the socket coupled to and suspendable from the residual limb. The dual skirts about the sleeve cooperate with the interior surface of the socket to form the seal and create a continuous connection along an upper margin of these skirts around the sleeve. The method further includes pushing air from the chamber through an expulsion valve coupled to an opening in the socket by inserting the residual limb into the socket and simultaneously and continually pulling air from the chamber through a vacuum pump coupled to an opening in the socket. Preferably, the air contained between the sleeve and the inner or lower skirt is removed by a "wicking" positioned therebetween. Suitable wicking can be an air permeable cotton sock fitted onto the residual limb over a portion of the sleeve.

DETAILED DESCRIPTION OF PRESENTLY PREFERRED EMBODIMENTS

Figure 1:
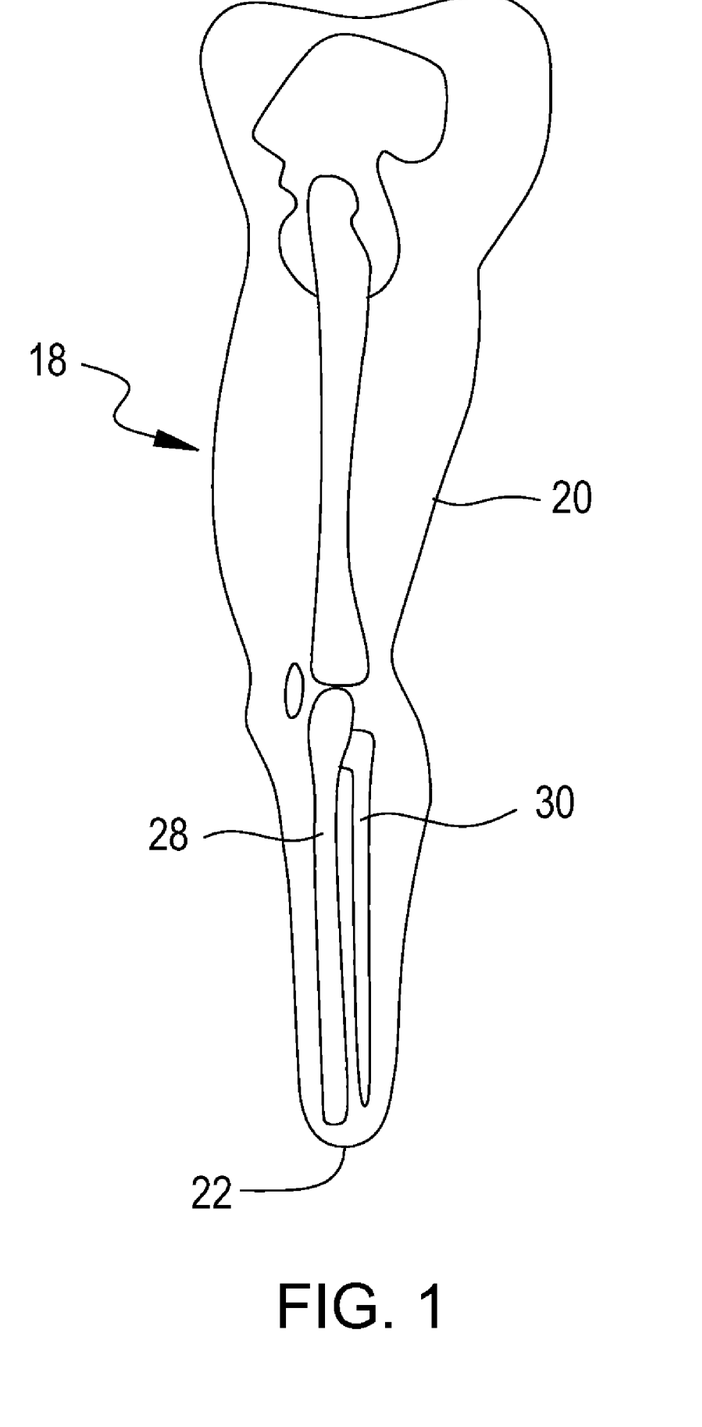
FIG. 1 is a side elevational view of the tissue and skeletal structure of an amputee's residual leg severed below the knee.
Figure 2:
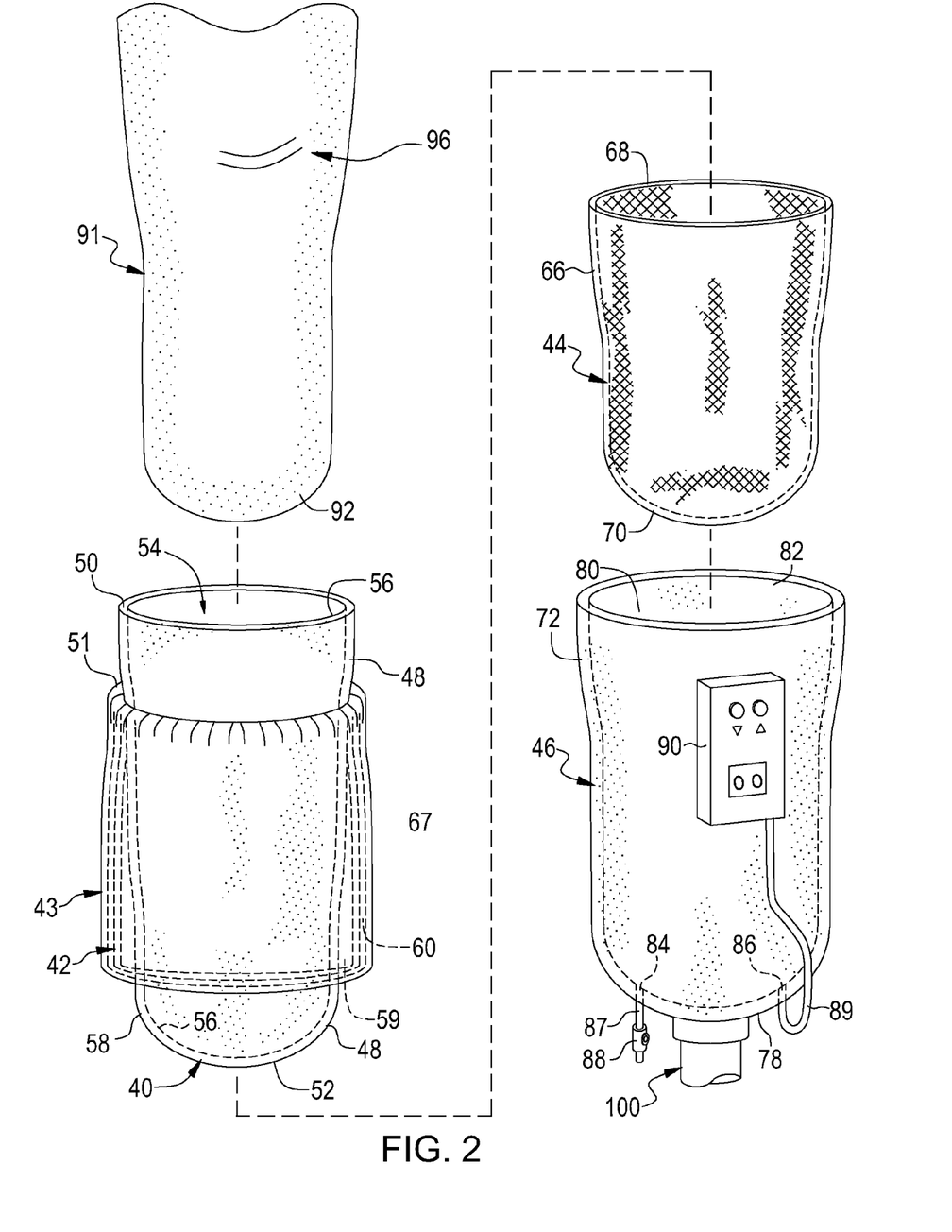
FIG. 2 is an exploded perspective view of a prosthetic sleeve and socket system in accordance with a preferred embodiment of the present invention.

FIG. 1 illustrates a below the knee residual limb 10 showing relatively low amount of residual flesh around the residual bone and potentially elongated portion. The present invention is illustrated in FIGS. 2-7, where like portions share like numbering. Generally, as illustrated in FIG. 2, the prosthetic sleeve and socket system of present invention includes a pliable, silicone sleeve 40 conformable to the shape of an amputee's residual limb, pliable, dual skirts or flaps 42,43 concentrically arranged about sleeve 40, an air wick 44 and a prosthetic socket 46 conforming to the shape of the amputee's residual limb. "Air wick" is hereby defined as an air permeable material, said material including air permeation characteristics in all directions. For example, a cotton sock would be one form of an air wick. The purpose of the air wick is to avoid the entrapment of air between sleeve 40 and socket 46 and to allow a smooth flow of air over all parts of the sleeve 40 to facilitate the creation of downward suction force caused by the manual insertion of a leg into socket 46 or a discrete vacuum pump 90.

Figure 3:
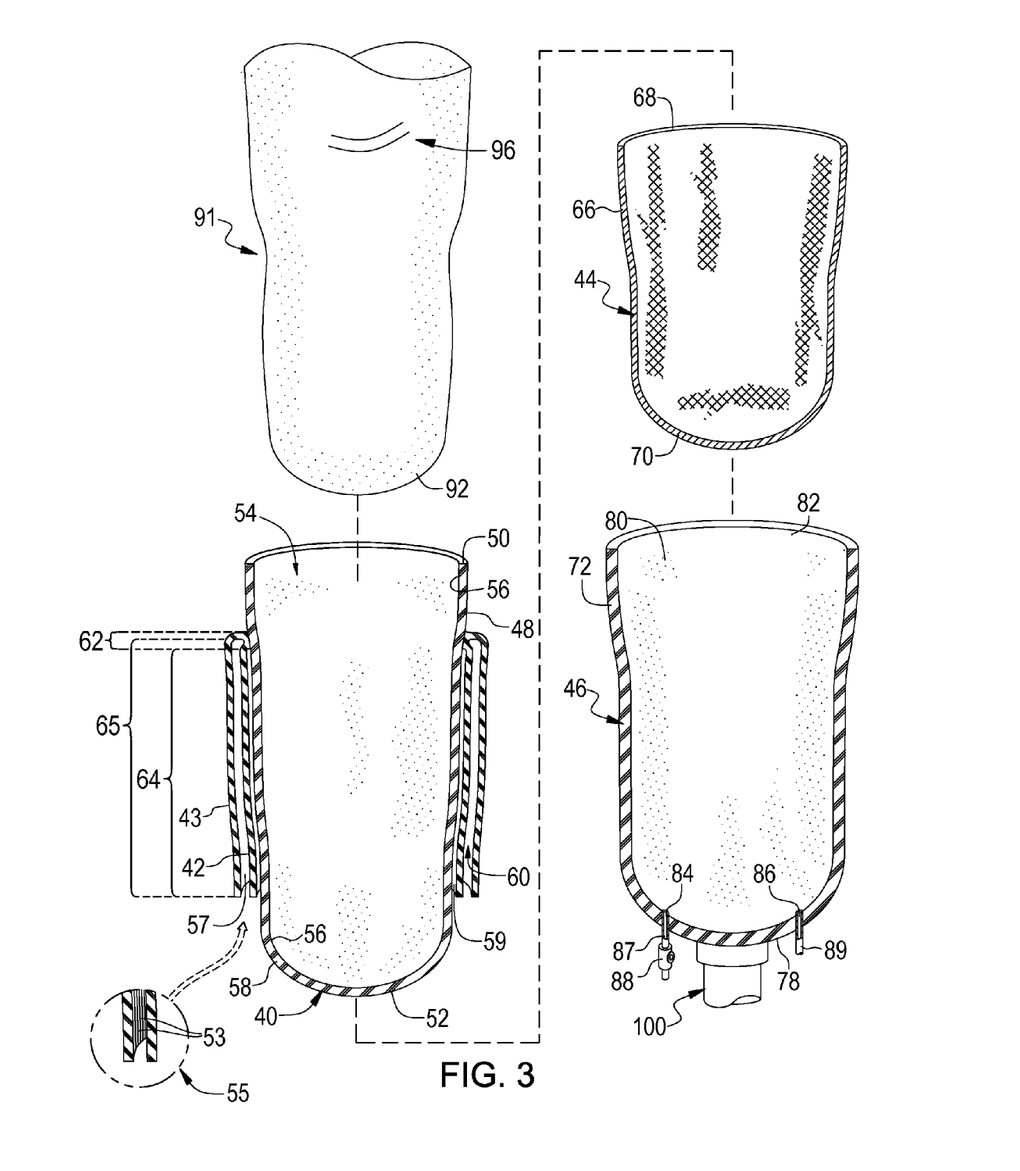
FIG. 3 is a cross-sectional view of the prosthetic sleeve and socket system of FIG. 2.

Referring also to FIG. 3, sleeve 40 includes a cylindrical, continuous sidewall 48 having an upper circumferential extent 50 and a closed bottom end 52. The sleeve 40 includes a limb receiving opening 54 defined and bounded by extent 50, an inner surface 56 of sleeve sidewall 48, and a closed bottom end 52. Since sidewall 48 and closed bottom 52 are constructed of pliable, silicone sheeting, sleeve 40 is sufficiently pliable to fit snuggly around an amputee's residual limb, whether it is an arm, leg, or other appendage. Preferably, sleeve sidewall 48 has a uniform thickness of between 3 mm to 6 mm and has surface characteristics that lends itself to comfortably gripping a user's skin.

Lower or inner skirt 42, which is positioned concentrically about sleeve 40, connects to and is fused with outer surface 58 of sleeve sidewall 48 at fused margin 62, and upper or outer skirt 43 connects to and is fused with outer surface 58 at the same point 62 in coextensive integration. Specifically, inner and outer skirts 42,43 consist of a substantially, tubular silicone sheet having an attached margin at 62 that defines the inner skirt proceeding directly downward therefrom and the outer skirt 43 arcing slightly over inner skirt 42 and downward. Inner skirt freely descends downward to define a free margin 64 and outer skirt descends a similar, but greater distance defining a free margin 65. The combination of both skirts extend over sleeve 40 an area equal to margin 61 (see FIG. 7) and define two continuous circumferential envelopes 59,60 underneath each free margin 64,65, respectively, with each skirt overlapping one another as shown.

Attachment of the skirts 42,43 at 62 to sidewall 48 is accomplished through either using an adhesive or by stitching, or producing sleeve 40 and skirts 42,43 as a single piece. Preferably, fused margin 62 is attached to sidewall 48 by affixing it directly on the outer surface 58 and allowing the skirts 42,43 to extending downward in the general direction of closed bottom 52, such that envelope spaces 59,60 are left between the two. In this manner each skirt 42,43 can be easily folded downward to lie against outer surface 58 of sidewall 48 without creating an otherwise bulky fold about fuse margin 62. Preferably, both skirts 42,43 have uniform thicknesses of between 1 mm and 3 mm, and preferably both skirts are integral with one another at the point of fusing 62.

As may be understood, while fused margin 62 is shown to be affixed to sleeve 40 at an approximate upper-point along sidewall 48, this fused margin may be moved up or down sleeve 40 to provide a variable placement of free margins 64,65, and the free margins 64,65 themselves may be varied by moving the point of fusing on the skirts 42,43 so that 42 and 43 may vary in length with respect to one another. Also, the width of fuse margin 62 itself may be varied. Such variations allow for the extension of these free upper margins over more surface area of sleeve wall 48 to allow for additional contact and stability of sleeve 40 over limb 91. In this manner, various sizes and configurations of sleeve 40 may be manufactured to fit various sizes and shapes of residual limbs, including residual limbs on arms, legs, fingers, etc. Similarly, various sizes and shapes of sockets 46 cooperatively shaped with sleeves 40 would be utilized to accommodate various shapes and sizes of residual limbs.

Figure 4:
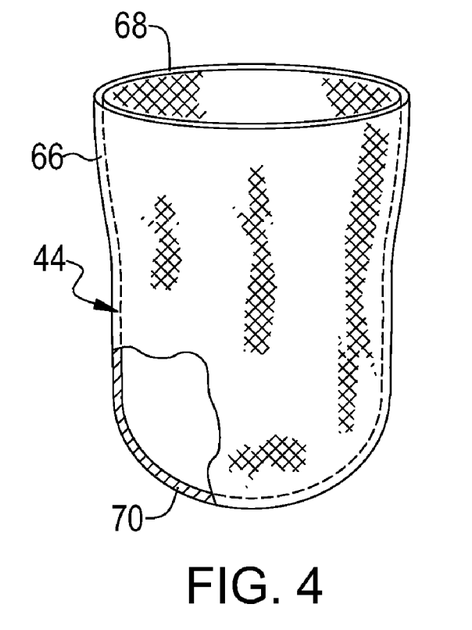
FIG. 4 is perspective view of an air wick in partial cross-section in accordance with the sleeve and socket system of FIG. 2.

Referring now to FIG. 4, air wick 44 is constructed of a thin, air permeable fabric formed into a sock. Wick 44 therefore includes a cylindrical continuous wall 66, an open top 68 and a closed bottom 70. It is preferred that wall 66 has a height substantially equal to the distance between the lowermost point of fused margin 62 plus gap 45 downward to closed bottom end 52 and covering same. This positions air wick 44 over bottom end 52 and sidewall 48 of sleeve 40, with wall 66 continuously extended between skirt 42 and outer surface 58 of sidewall 48 when skirt 42 is pressed against sleeve 40. Hence, wick 44 fills envelope 59 when inserted into socket 46 as will be discussed.

While not shown, the inventors contemplate the usage of a similar portion of an air wick shaped into a tube or cylinder and configured to fill envelope 60 of outer skirt 43 between the lowermost point of fused margin 62 to the lowermost extent of skirt 42. While this type of tubular wick configuration is sufficient to avoid the entrapment of air within envelope 60 during donning of the invention upon a residual limb, it may be preferable, and simpler, to utilize an integrally formed vertically oriented series of parallel ridges 53 (see inset 55 of FIG. 3) formed upon the inner surface 57 of the free margin portion 64 of outer skit 43. Such ridges would necessarily create a series of vertical air channels, thereby facilitating the escape of air from underneath free margin portion 65 upon donning. Irrespective of the inclusion of these additional wicking elements, the lack of a wicking structure between skirts 42 and 43 does not substantively impair the operation of the invention.

Figure 5:
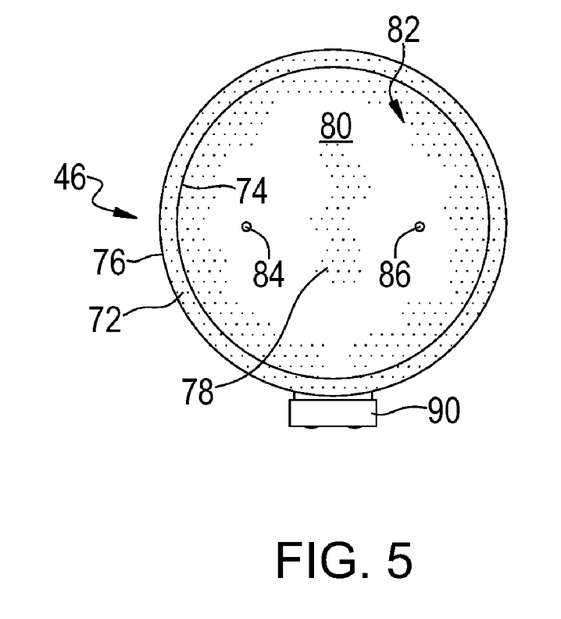
FIG. 5 is a plan view of the open end of the socket of FIG. 2.

Referring to FIG. 5, socket 46 is composed of a socket wall 72 having an interior surface 74 and an exterior surface 76 and a socket distal end 78. Socket distal end 78 merges integrally into socket wall 72 at the lower end of the wall. Jointly with the interior surface 74, distal end 78 forms a substantially cup-shaped inner volume 80 which is accessible through a proximal residual limb insertion opening 82 at the proximal end. Since socket 46 is configured to attach to an amputee's residual limb by a partial vacuum it is a so-called suction-socket.

A pair of openings 84 and 86 are formed through socket distal end 78 for allowing air within inner volume 80 to selectively escape from inner volume 80 ahead of an amputee's residual limb 91 when the latter is inserted into inner volume 80 up to but below the knee 96. In particular, opening 84 is coupled to a selectively actuated expulsion valve 88 for allowing air under pressure to exit inner volume 80 via short conduit 87. An example expulsion valve suitable for use in the herein described system is a V4 or V5 expulsion valve offered by Otto Bock HealthCare, Inc. Opening 86 is connected to a vacuum source 90 via line 89 for pulling air out of inner volume 80 to form a partial vacuum. Vacuum source 90 is preferably self-contained and includes a power source, a release valve, a vacuum pump and a pressure control means configured to maintain pressure within inner volume 80 at a predetermined pressure. An exemplary vacuum source includes the "eVAC" model no. DF-100 manufactured by Smith Global, located in Laurie, Mo.

Figure 6:
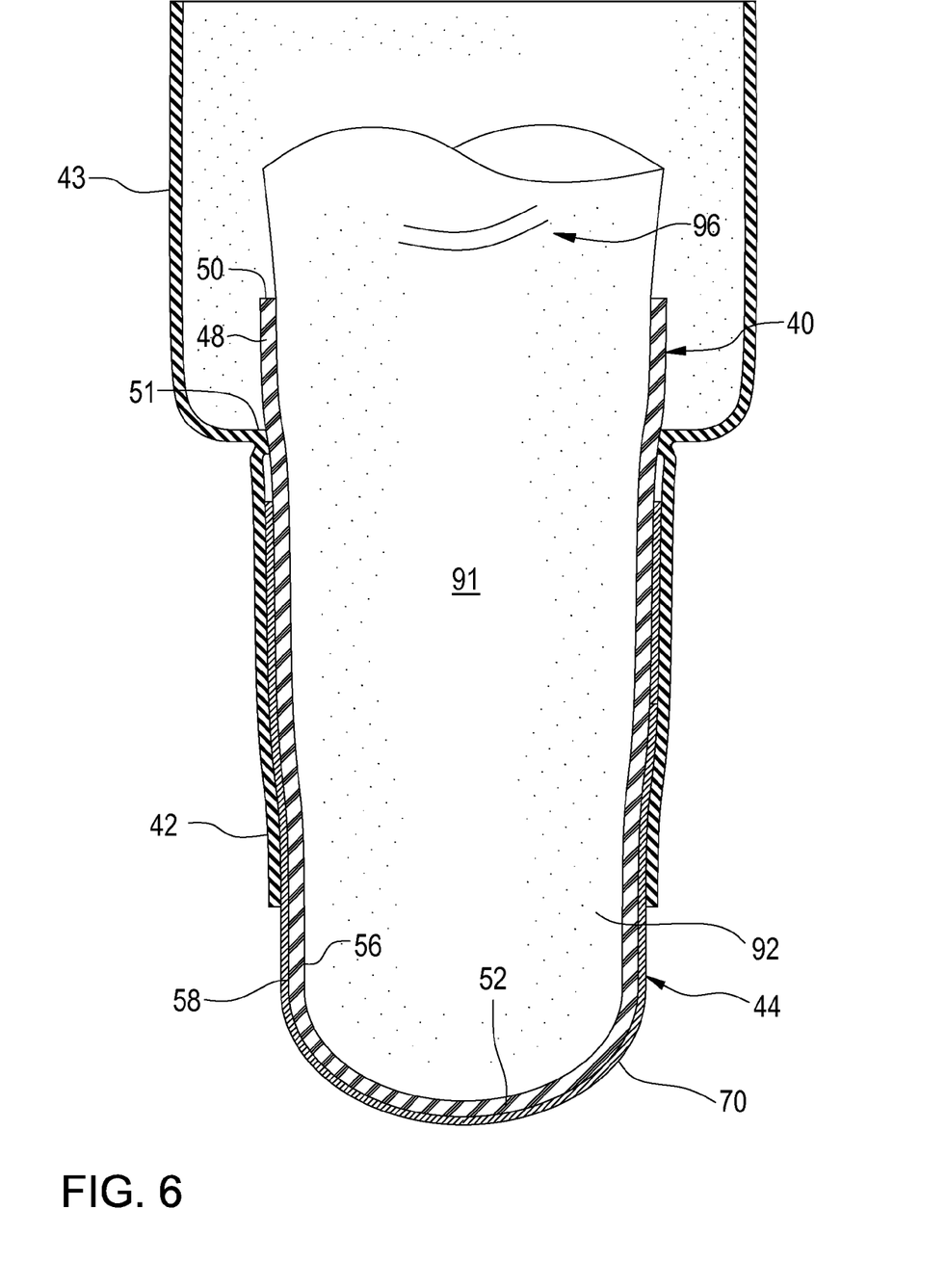
FIG. 6 is a cross-sectional view of the sleeve and socket system of FIG. 2 suspended from an amputee's residual leg below the knee and showing the inner or lower skirt against the liner and the outer or upper skirt manipulated up and away from the sleeve; and, FIG. 7 is a cross-sectional view of the sleeve and socket system of FIG. 6 illustrating formation of a seal between the sleeve and socket during installation upon a residual limb.

Referring to FIG. 6, there is shown the prosthetic sleeve and socket system of the present invention suspended from a leg severed below the knee near the upper ankle. An amputee's severed or residual limb 91 includes a lower end 92 that is inserted through upper circumferential extent 50 and into limb receiving opening 54 of sleeve 40. Lower end 92 of the amputee's limb is fully engaged with inner surface 56 of sleeve sidewall 48 and closed bottom end 52, with sidewall 48 exerting pressure against the leg sufficient to maintain sleeve 40 suspended from lower end 92 of the amputee's limb when sleeve 40 is coupled to socket 46 and the desired prosthetic appendage 100. The diameter and length of sleeve 40 are determined based upon the length and diameter of lower end 92 and the amount of flesh present about lower end 92. The amount of flesh present can also dictate the thickness of sleeve sidewall 48 since the abundance or lack of flesh can determine how well sleeve 40 engages and remains engaged with socket 46. For example, in those instances where sleeve 40 and socket 46 are to be coupled with a leg severed below the knee the thickness of sleeve sidewall 48 may be increased to make up for the lack of flesh typically found about that part of the leg. Alternatively, when sleeve 40 and socket 46 are to be placed on a leg severed above the knee, the thickness of sleeve sidewall 48 may be less since the upper leg typically includes a relatively substantial amount of flesh.

With sleeve 40 positioned on lower end of the residual limb 91, air wick 44 is then positioned over closed bottom end 52 of sleeve 40 with closed bottom 70 of wick 44 being located adjacent to and in contact with closed bottom end 52. Further, wick 44 extends upwardly along sleeve sidewall 48 to a point near fused margin 62, having an upper extent 51, but leaving a slight gap 45 (see FIG. 7). Skirt 43 to this point may be positioned up and out of the way of wick 44 and skirt 42 to facilitate their smooth integration. This allows easy manipulation of skirt 42 downward to lie flat against the outer surface of air wick 44 along inner skirt 42's interior surface, and prevents almost all direct contact between the sidewall 48 and skirt 42. Once wick 44 and skirt 42 are smoothly secured against sleeve 40, skirt 43 may be folded down and manipulated to smoothly flow over skirt 42 to a form as shown in FIG. 7.

Figure 7:
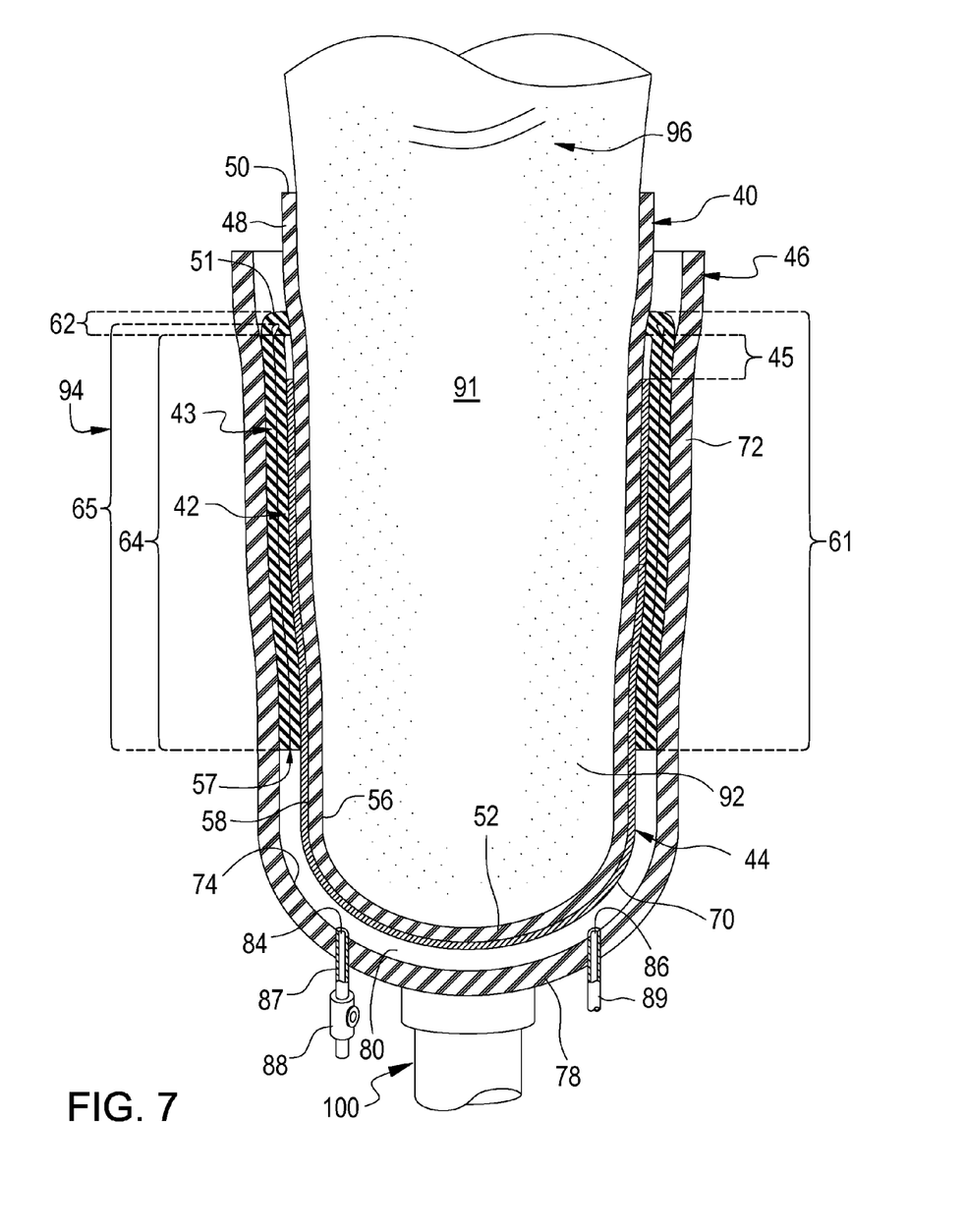

Referring now to FIG. 7, the lower end of the amputee's residual leg 91, along with sleeve 40 and air wick 44, are positioned within inner volume 80 of socket 46. In particular, closed bottom 70 of wick 44, along with sleeve 40, is positioned immediately above distal end 78 of socket 46 with sleeve sidewall 48 being located substantially parallel to socket sidewall 72. As is now apparent, skirt 42 is first manipulated to lie flat against and between interior surface 74 of socket 46 and air wick 44, and skirt 43 is similarly manipulated to lie flat against skirt 42 outer surface and in between interior socket surface 74 and skirt 42. If desirable, the vertical channels formed on the inner surface of outer skirt 43 will now lie flat against the outer surface of skirt 42, thereby creating a series of vertical air passages between each skirt such that air entrapment is prevented therebetween. The interaction of skirts 42,43 with interior surface 74 acts to create a double continuous seal 94 between sleeve 40 and socket 46 along margin 65. Seal 94 therefore encloses inner volume 80 within socket 46, defining inner volume 80 by interior surface 74, skirts 42,43, and sleeve sidewall 48.

The seal 94 is first created when skirt 42 is initially inserted into inner volume 80. This occurs as soon as skirt 42 makes a continuous connection with interior surface 74 of socket 46 with skirt 43 also making a continuous connection to the inner surface of skirt 43. Thus, as sleeve 40 and skirts 42,43 are pressed into inner volume 80, seal 94 is created, maintained and moved downwardly toward distal end 78 thereby causing the air within socket 46 to be compressed. This further helps to press skirts 42,43 against interior surface 74 thus strengthening the interaction between skirts 42,43 and socket 46 and ultimately seal 94. Once the air reaches a predetermined pressure, the compressed air is allowed to escape from inner volume 80 through opening 84 and expulsion valve 88. Expulsion valve 88 typically includes a small manual release to control the timing and volume of air that might be expelled through it. Air can also escape through a release valve contained within vacuum source 90, if present, but vacuum source 90 itself will tend to evacuate the air held by seal 94 in response to and at a rate characterized by the operational specifications of the vacuum unit. By increasing the number of openings through which the compressed air can be selectively evacuated from inner volume 80, sleeve 40 is more easily inserted into and coupled with socket 46 since the compressed air can escape at a faster rate. Hence, it is anticipated that multiple expulsion orifices and vacuum conduit openings might be incorporated into the socket 46.

Once lower end 92 of the amputee's residual limb, along with sleeve 40 and air wick 44, are fully seated within inner volume 80 of socket 46, a partial vacuum is created within inner volume 80. In particular, vacuum source 90 acts to pull air within inner volume 80 out of socket 46 through opening 86 to create a regulated partial vacuum. Since air wick 44 is provided between skirt 42 and sleeve sidewall 48, and, if desired, the air channels that separate skirts 42 and 43, the air located between these elements is more easily removed from inner volume 80. By interposing the air wick 44 along the entire surface of sleeve 40, up to skirt fuse juncture 62 between skirt 42 and the sleeve 40 as shown, and including any vertical air channels, pockets of isolated air are avoided in envelopes 59 and 60 so that the full retention force of the created vacuum extends along the entire outer surface 58 of sleeve 40 such that socket 46 and residual limb 91 are continuously drawn together. The retention of a vacuum attraction between socket 46 and limb 91 allows socket 46 to be of a substantially reduced size over conventional sockets and permits, in many cases, the disposal of bulky suspending straps.

As will be apparent to one skilled in the art, various modifications can be made within the scope of the aforesaid description. Such modifications being within the ability of one skilled in the art form a part of the present invention and are embraced by the claims below. For example, air wicking, that ensures air permeation over the entire surface area 58 of sleeve 40, is currently satisfied through the utilization of a sock placed over sleeve 40. However, the inventor envisions that other structures may be employed to promote air permeation and avoid the creation of air pockets over the surface area of sleeve 40. Surface texture and molded structures in the surface 58 of sleeve 40 may be employed to promote air permeation across surface 58. Further, intervening substances, such as granularized powders, might also be employed to promote air permeation. Similarly, various textures, molded structures, and substances may be interspersed between skirts 42,43 to facilitate air removal.

The invention claimed is:

1. An apparatus for attaching a prosthetic to a residual limb, comprising:
   a. means for surrounding a lower portion of said limb with material;
   b. first means depending downward from an upper portion of said surrounding means for circumferentially covering said same;
   c. second means depending downward from an upper portion of said surrounding means for circumferentially covering said same, wherein said second means is positioned above and overlapping said first means;

d. first permeation means interposed between said surrounding means and said first means for permeating air between said outer surface of said surrounding means and said first means;

e. second permeation means interposed between said first means and said second means for permeating air between them;

f. a prosthetic socket positioned over said surrounding means and said first and second means such that an airtight seal is created between said socket and surrounding means;

g. said socket including means for expelling air from an interior of said socket; and, h. said socket also including means for connecting an interior of said socket with an exterior vacuum source.

2. The apparatus as recited in claim 1, wherein said socket is adapted to fit over a residual limb selected from a group consisting of a residual limb above the knee, a residual limb below the knee, a residual limb above the elbow, and a residual limb below the elbow.

3. The apparatus as recited in claim 2, wherein said first permeation means comprises a fabric sock adapted to slide over said surrounding means.

4. The apparatus as recited in claim 3, wherein said apparatus further comprises a prosthetic limb depending from said socket.

5. The apparatus as recited in claim 4, further comprising an upper margin on said material means and wherein said first and second means attach to said surrounding means at said margin.

6. The apparatus as recited in claim 1, wherein said first permeation means comprises molded surface features on at least one of said first or second means.

7. An apparatus for attaching a prosthetic to a residual limb, comprising:
   a. a sleeve for surrounding a lower portion of said limb, said sleeve having an outer surface;
   b. a first circumferential skirt depending downward from an upper portion of said sleeve, said first circumferential skirt including a fused margin affixing said same onto said sleeve;
   c. a second circumferential skirt depending downward from an upper portion of said sleeve, said second circumferential skirt affixed said sleeve at said fused margin, wherein said first and second skirts overlap and second skirt includes means for permeating air between said two skirts;
   d. wherein said outer surface of said sleeve includes surface features to permit permeation of air between said outer surface of said sleeve and said first skirt;
   e. a prosthetic socket positioned over said sleeve and said skirts such that a airtight seal is created between said socket and said sleeve;
   f. said socket including an expulsion valve at a lower point thereof; and,
   g. said socket including a vacuum port in a lower portion thereof, said port connected to a vacuum source.

8. The apparatus as recited in claim 7, wherein said socket is adapted to fit over a residual limb selected from a group consisting of a residual limb above the knee, a residual limb below the knee, a residual limb above the elbow, and a residual limb below the elbow.

9. The apparatus as recited in claim 8, wherein said apparatus further comprises a prosthetic limb depending from said socket.

10. The apparatus as recited in claim 9, wherein said skirts depend from said sleeve downward an equal length.

11. The apparatus as recited in claim 10, further comprising a vacuum pump connected to said vacuum port and positioned on said socket.

12. An apparatus for attaching a prosthetic to a residual limb, comprising:
   a. a sleeve for surrounding a lower portion of said limb, said sleeve having an outer surface;
   b. a first circumferential skirt depending downward from an upper portion of said sleeve;
   c. a second circumferential skirt depending downward from an upper portion of said sleeve, wherein said first and second skirts overlap;
   d. first a fabric sock positioned between said sleeve and said first skirt for permeation of air between said outer surface of said sleeve and said first skirt, said fabric sock adapted to slide over said sleeve;
   e. a prosthetic socket positioned over said sleeve and said skirts such that a seal is created between said socket and said sleeve, wherein said socket is adapted to fit over a residual limb selected from a group consisting of a residual limb above the knee, a residual limb below the knee, a residual limb above the elbow, and a residual limb below the elbow;
   f. said socket including an expulsion valve at a lower point thereof;
   g. said socket including a vacuum port in a lower portion thereof, said port connected to a vacuum source; and,
   h. wherein said apparatus further comprises a prosthetic limb depending from said socket.

13. An apparatus for attaching a prosthetic to a residual limb, comprising:
   a. a sleeve for surrounding a lower portion of said limb, said sleeve having an outer surface;
   b. a first circumferential skirt depending downward from an upper portion of said sleeve;
   c. a second circumferential skirt depending downward from an upper portion of said sleeve, wherein said first and second skirts overlap;
   d. first means positioned between said sleeve and said first skirt for permeation of air between said outer surface of said sleeve and said first skirt;
   e. a prosthetic socket positioned over said sleeve and said skirts such that a airtight seal is created between said socket and said sleeve;
   f. said socket including an expulsion valve at a lower point thereof;
   g. said socket including a vacuum port in a lower portion thereof, said port connected to a vacuum source; and,
   h. further comprising a second permeation means on said second skirt for allowing the permeation of air between said first skirt and said second skirt.

14. An apparatus for attaching a prosthetic to a residual limb, comprising:
   a. a sleeve for surrounding a lower portion of said limb, said sleeve having an outer surface;
   b. a first circumferential skirt depending downward from an upper portion of said sleeve;
   c. a second circumferential skirt depending downward from an upper portion of said sleeve, wherein said first and second skirts overlap;
   d. a plurality of vertical channels positioned between said first and second skirts on the inside surface of said second skirt for permeation of air first and second skirts;
   e. a prosthetic socket positioned over said sleeve and said skirts such that an airtight seal is created between said socket and said sleeve;

f. said socket including an expulsion valve at a lower point thereof; and, g. said socket including a vacuum port in a lower portion thereof, said port connected to a vacuum source; and, h. wherein said first permeation means comprises said plurality of vertical channels on the inside surface of said second skirt.

15. A method of attaching a prosthesis to a residual limb utilizing an apparatus comprising:
   i. a first pliable sleeve;
   ii. a second pliable sleeve concentrically positioned about said first sleeve;
   iii. a third pliable sleeve concentrically positioned about said first sleeve and said second sleeve;
   iv. wherein said first, second, and third sleeves are configured for cooperating with an interior surface of said prosthetic socket and forming a sealed chamber contained between said residual limb and said socket; and,
   v. wherein said second and third sleeves comprise a continuous circumferential sheet, said sheet including an upper fused margin attached to said first sleeve; and
   vi. wherein said residual limb includes a proximal end and a distal end;
   said method comprising the steps of:
   a. placing said first pliable sleeve about said residual limb;
   b. manipulating said second and third pliable sleeves to position each toward said proximal end;
   c. placing an air wick over said first pliable sleeve to substantially cover said residual limb distal end;
   d. manipulating at least one of said sleeves to substantially cover said air wick;
   e. manipulating said remaining sleeves to substantially overlap said other sleeve substantially coving said air wick;
   f. inserting said covered residual limb into a prosthetic socket conforming to the shape of said residual limb while maintaining the configuration achieved in the prior steps a through e;
   g. forming a continuous seal between said sleeves and an interior surface of said socket such that an isolated vacuum vessel is formed between said socket and said sleeves; and
   h. evacuating air from said vessel such that a suction attraction between said residual limb and said socket is maintained;
   i. wherein one of said sleeves is arranged above said other sleeves and said step of manipulating said remaining sleeve to substantially overlap said other sleeve substantially covering said air wick comprises pulling said sleeve positioned above said other sleeves down over the other sleeve;
   j. wherein one of said sleeves in said step of arranging one of said sleeves above the other sleeves includes a plurality of air channels on a side facing said other sleeves such that air may be drawn out from between said sleeves.

16. A method of attaching a prosthesis to a residual limb utilizing an apparatus comprising:
   (i) a first pliable sleeve;
   (ii) a second pliable sleeve concentrically positioned about said first sleeve;
   (iii) a third pliable sleeve concentrically positioned about said first sleeve and said second sleeve;
   (iv) wherein said first, second, and third sleeves are configured for cooperating with an interior surface of said prosthetic socket and forming a sealed chamber contained between said residual limb and said socket; and,
   (v) wherein said second and third sleeves comprise a continuous circumferential sheet, said sheet including an upper fused margin attached to said first sleeve;
   (vi) wherein said residual limb includes a proximal end and a distal end; said method comprising the steps of:
   a. placing said first pliable sleeve about said residual limb;
   b. manipulating said second and third pliable sleeves to position each toward said proximal end;
   c. placing an air wick over said first pliable sleeve to substantially cover said residual limb distal end;
   d. manipulating at least one of said sleeves to substantially cover said air wick;
   e. manipulating said remaining sleeves to substantially overlap said other sleeve substantially coving said air wick;
   f. inserting said covered residual limb into a prosthetic socket conforming to the shape of said residual limb while maintaining the configuration achieved in the prior steps a through e;
   g forming a continuous seal between said sleeves and an interior surface of said socket such that an isolated vacuum vessel is formed between said socket and said sleeves;
   h. evacuating air from said vessel such that a suction attraction between said residual limb and said socket is maintained; and,
   i. wherein said second sleeve to be positioned over said air wick includes a plurality of air channels formed on a side facing said first sleeve, and wherein said steps of placing an air wick over said distal end and manipulating said second sleeve over said air wick are replaced with the step of manipulating said second sleeve over said distal end such that said plurality of air channels are positioned between said second sleeve and said first sleeve so that air between said first and said second sleeves may be freely drawn out.

* * * * *